United States Patent [19]

Plesset et al.

[11] 4,409,982
[45] Oct. 18, 1983

[54] ULTRASONIC STEP SCANNING UTILIZING CURVILINEAR TRANSDUCER ARRAY

[75] Inventors: Kiven Plesset, Wallingford; Darwin P. Adams, Guilford, both of Conn.

[73] Assignee: Picker Corporation, Cleveland, Ohio

[21] Appl. No.: 198,436

[22] Filed: Oct. 20, 1980

[51] Int. Cl.³ ............... G01N 29/04; A61B 10/00
[52] U.S. Cl. ........................ 128/660; 73/626
[58] Field of Search ............... 73/618–620, 73/622–623, 625–626, 627–628, 642; 128/660–663; 367/88, 103, 105, 119, 122, 153–154

[56] References Cited

U.S. PATENT DOCUMENTS

| | | | |
|---|---|---|---|
| 3,532,382 | 1/1971 | Mount | 73/628 X |
| 3,771,354 | 11/1973 | Miller | 73/625 |
| 3,938,502 | 2/1976 | Bom | 128/660 |
| 4,070,905 | 1/1978 | Kossoff | 73/626 X |
| 4,207,621 | 6/1980 | Clearwaters et al. | 367/153 X |
| 4,228,687 | 10/1980 | Fraser | 73/628 X |
| 4,233,678 | 11/1980 | Brady | 367/122 |
| 4,241,611 | 12/1980 | Specht et al. | 128/660 X |
| 4,271,490 | 6/1981 | Minohara et al. | 367/122 |
| 4,281,550 | 8/1981 | Erikson | 73/642 X |
| 4,344,327 | 8/1982 | Yoshikawa et al. | 128/661 X |

FOREIGN PATENT DOCUMENTS

| | | | |
|---|---|---|---|
| 2719130 | 1/1978 | Fed. Rep. of Germany | 73/618 |
| 1437486 | 5/1976 | United Kingdom | 128/660 |

OTHER PUBLICATIONS

Lancee, C. T. et al., "Construction of Circular UTS Array", Conf. Proc. 2d Europ. Cong. on UTS in Med., Munich, May 12–16, 1975, pp. 49–53.
Bom, N. et al., "An UTS Cardiac Scanner", Ultrasonics, Mar. 1972, pp. 72–76.

*Primary Examiner*—Kyle L. Howell
*Assistant Examiner*—Francis J. Jaworski
*Attorney, Agent, or Firm*—Watts, Hoffmann, Fisher & Heinke Co.

[57] ABSTRACT

An electronically step scanned real time ultrasonic imaging system and method is disclosed. The system includes a transducer assembly having an array of elements, each with an axis of transmission along which it transmits its main ultrasonic energy when electrically stimulated. The elements are disposed in a curvilinear array, wherein their axes of transmission are approximately coplanar, but divergent in the common plane. This configuration provides a relatively large scanned area without need for either electronic or mechanical sector scanning techniques to steer the incident ultrasonic energy over a large angle.

5 Claims, 6 Drawing Figures

ULTRASONIC STEP SCANNING UTILIZING CURVILINEAR TRANSDUCER ARRAY

TECHNICAL FIELD

This invention relates to the field of ultrasonic imaging equipment, and more particularly to an ultrasonic medical diagnostic system employing an improved transducer assembly and examination method.

BACKGROUND ART

In recent years, the field of diagnostic ultrasound has seen the emergence of a so called "real time" ultrasonic B scanning examination system. The term "real time" means that the systems produce successive images at a rapid enough rate so that images are generated faster than the retention rate of the human eye so that moving objects appear in continuous motion. Thus, in real time operation, the course of the study can be influenced by the operator contemporaneously with the actual study, based on his observation of the rapidly produced image succession. This real time feature is considered an improvement over previous forms of ultrasonic examination, in which only a single image is developed slowly and gradually during the course of a study by moving a single transducer about the patient's skin. In addition to allowing the operator to influence the course of the study, real time systems allow for "stop action" images of moving body parts, and also for motion studies.

Real time ultrasonic examination systems have mainly fallen into two general types, i.e., linear scanning and sector scanning. Electronic linear scanning systems utilize a transducer assembly including a large linear array of individual piezoelectric ultrasonic transducer elements. Imaging circuitry fires a succession of different groups of elements in accordance with a predetermined repeated sequence. This produces a succession of resultant ultrasonic beams propagated along respective parallel paths extending outwardly from the transducer assembly. The assembly is held stationary against the patient's body during image generation.

This technique, in conjunction with known forms of imaging circuitry and display apparatus, produces from received ultrasonic echoes information defining a two dimensional rectangular image of the internal body structure of the patient taken in a common plane, or "slice" through part of the body near the transducer array. One coordinate of each point on the image plane is determined by the amount of time required for incident ultrasonic energy to be reflected back to the transducers from a tissue interface within the body. The other coordinate is determined by the location, along the transducer array, of the axis of the resultant ultrasonic beam which caused the reflected energy.

By operating this system to repeatedly step the incident beam origin along the linear transducer array at, for example, thirty repetitions per second, the rapid sequence of ultrasonically produced image frames which result can show motion of a moving body part. Alternately, a single frame of image data can be held for display, in order to stop rapid motion of such a body part.

The display area scanned by such linear step scanners is rectangular and suitable for presentation on a two dimensional display system, such as a CRT. The electronics required for such a system are relatively inexpensive and simple, since all the beams are parallel and stepped over uniform increments. Moreover, linear stepped scanning systems exhibit substantially uniform field of view throughout their display area.

Linear systems, however, do have some disadvantages. For example, the transducer assembly must of necessity be rather long, and therefore clumsy to use, since the length of one side of the rectangular display equals the length of the transducer array. Since all the ultrasonic beams produced by the linear scanner are propagated along parallel lines, the linear scanner is not generally capable of imaging portions of the patient's body which are hidden behind other nearer portions, such as an organ which may be located behind a rib.

A known type of electrically stepped linear array ultrasonic system is described in the following publication, which is hereby expressly incorporated by reference: Havlice, J. F., et al, "Medical Ultrasonic Imaging: An Overview of Principles and Instrumentation," Proceedings of the IEEE, Vol. 67, No. 4, April, 1979, pp. 620–641.

Another type of known real time electronic ultrasonic scanner is the electronic sector scanner. In such devices, a linear array of transducer elements is employed as in the case of linear step scanning. The length of the array, however, is considerably shorter than in the case of the step scanned linear device described above.

In using the electronic sector scanner, the transducer assembly is held stationary near the portion of the patient's body to be examined. All elements are repeatedly fired in a single group. Phase delay circuitry is associated with imaging circuitry which is utilized to control ultrasonic beam emission and reception by the transducer elements. By proper phase delay of respective elements, the ultrasonic beam repeatedly produced by the transducer array is "steered" at different angles to the face of the transducer assembly. The angle of the ultrasonic beams produced by successive firings of all the elements of the transducer array is repeatedly scanned in increments from one side to another, such that the successive ultrasonic beams collectively sweep through the patient's body at different angles in a common plane.

Several advantages over the linear stepped scanner are achieved by use of the electronic sector scanner. First, the transducer assembly is significantly more compact than in the case of the stepped scanner, and can thus be used at almost any location on the patient's body. Since the ultrasonic beams are directed into the subject at different angles, the electronic sector scanner can image portions of the body which might be hidden from view of the linear stepped scanner because of their location behind other more opaque portions of the body, such as bone.

Electronic sector scanning, however, does have its own inherent disadvantages. One such disadvantage is that these scanners have a narrow field of view in regions of the body close to the transducer assembly. This is because the field of view of the sector scanner resembles a sector of a circle and, close to the transducer assembly, the excursion of the sweep of the ultrasonic beam is quite small.

Another disadvantage of the electronic sector scanner is the relatively high cost of such units, due in large measure to the complexity of the electronics necessary to achieve the delay scheme employed to effect beam steering. While a typical linear transducer step scanner costs in the neighborhood of $15,000 to $30,000, the corresponding range of cost for electronic sector scanners is about $65,000 to $100,000 each.

Mechanically steered real time linear and sector scanners, using oscillating or rotating single crystal transducers, have also been proposed. Such systems, however, suffer from relatively large physical size, and problems associated with reliability of the mechanical drive. They also usually require the transducer to be immersed in a fluid.

Known proposals for electronic and mechanical sector scanners are described in the above referenced Havlice, et al., publication.

Another system, a variant of ultrasonic step scanning, (Bushmann "New Equipment and Transducers for Ophthalmic Diagnosis," *Ultrasonics*, Vol. 3, pages 18 et seq, January–March, 1965,) has been proposed relating to ultrasonic examination of the eye. It is suggested to ultilize ten transducers arranged in an arc such that the ultrasonic beams emitted by each of the transducers mutually converge near the center of the eye ball. Pulsing circuitry is applied to separately fire each of the transducers in a sequence.

A disadvantage of this type of examination stems from the fact that tissue interface points within the patient's body which generate ultrasonic echoes may be struck by primary incident energy from more than one transducer. Each such point could thereby lack uniqueness of location on the image display, causing blurring.

This lack of unique location of multiply-struck interface points would be caused by inhomogeneity in the patient's body. Acoustic velocity differs among tissue types. If the time required for an ultrasonic echo from one transducer to return to that transducer from the subject point is different from the corresponding return time with respect to another transducer whose energy also strikes the point, the subject point will show up at slightly different spots on the display.

It is an object of this invention to provide an ultrasonic scanning system having the flexibility, compactness and swept beam characteristics of an electronic sector scanner without the sector scanner's limited close up field of view and high price, while preserving the uniqueness of display location for each imaged point, all for roughly the cost of a simple linear step scanner.

DISCLOSURE OF INVENTION

The ultrasonic scanning system of this invention overcomes or reduces the disadvantages of the stepped linear scanner as well as those of the electronic and mechanical sector scanners, while combining advantages of both.

A system embodying this invention includes an ultrasonic transducer element array, and imaging electronics coupled to actuate the transducer array for emitting incident ultrasonic energy and to convert received echoes to electrical signals. The system also includes appropriate display apparatus to convert the electrical signals to a visual image describing internal structure of the patient's body.

The transducer array has a curvilinear arrangement of its elements. The transducer elements are disposed with their axes of primary transmission being divergent within a commmon plane. This feature enables the system to direct ultrasonic energy beams into a patient's body at different angles depending on which elements are fired. This facilitates the obtaining of ultrasonic echoes from body tissue interfaces located behind body parts which would obscure such interfaces if the ultrasonic beams were parallel. The divergent beams also provide a larger imaged area than would exist with a linear scanner employing the same length array.

In accordance with a more specific aspect of the invention, imaging electronics is provided for repeatedly firing the transducer elements in a sequence of groups to effect step scanning of the ultrasonic energy along the array for real time ultrasonic imaging. This feature enables the system to produce a series of resultant ultrasonic beams which sweep across the subject repeatedly and in a succession of varying angles, similar to the beam sweeping operation of an electronic sector scanner. Due to the fact that the sweeping, or angle changes, is effected by firing the elements in steps along the length of the curvilinear array, similarly to a linear scanner, rather than by means of complex delay timing techniques, the beam sweeping motion of the present system is obtained with electronics far simpler and less expensive than in the electronic sector scanner.

Moreover, since the resultant ultrasonic beams are emitted from spaced points along the curvilinear array, rather than being generated from a common origin, as in the case of the electronic sector scanner, field of view close to the array is improved over that of the sector scanner.

The curvilinear configuration disposing the respective beam axes at divergent angles to one another also prevents the difficulties encountered in the use of curved arrays wherein the beam axes converge. No single tissue interface location can be directly impinged upon by primary ultrasonic energy from more than one ultrasonic beam. Hence, each image point is indicated on the display as having a unique location.

The advantages of these features and the operation of this scanner are obtained with a transducer array which is sufficiently compact to permit applicability for use on nearly any part of the human body. This obviates the previous difficulty associated with linear step scanners generating parallel beams, wherein the actual array length must correspond to a dimension of the imaged area.

In accordance with other more specific features of this invention, the system can be equipped with delay control circuitry for focusing the transmitted ultrasonic energy at a predetermined distance from the transducer array face. Alternately, or in addition, the delay circuitry may be operated in the receive mode, in order to enhance detection of reflections from particular reception focal zones at a predetermined distance from the transducer assembly.

Additionally, the reception focusing circuitry may be of the dynamic focusing variety, wherein the reception focal zone is changed with time to recede outwardly into the subject to track the propagation of ultrasonic energy into the body.

According to another specific inventive feature, the transducer assembly is configured as a curvilinear convex array, wherein the assembly face defines an arc of a circle, and is approximately 5 centimeters in length, having about 76 ultrasonic transducer elements equally spaced along that length. This specific configuration is believed to be effective in medical diagnostic work.

These and other features of this invention will be understood in greater measure by reference to the following detailed description, and to the drawings, in which:

BEST MODE FOR CARRYING OUT THE INVENTION

Figure 1:
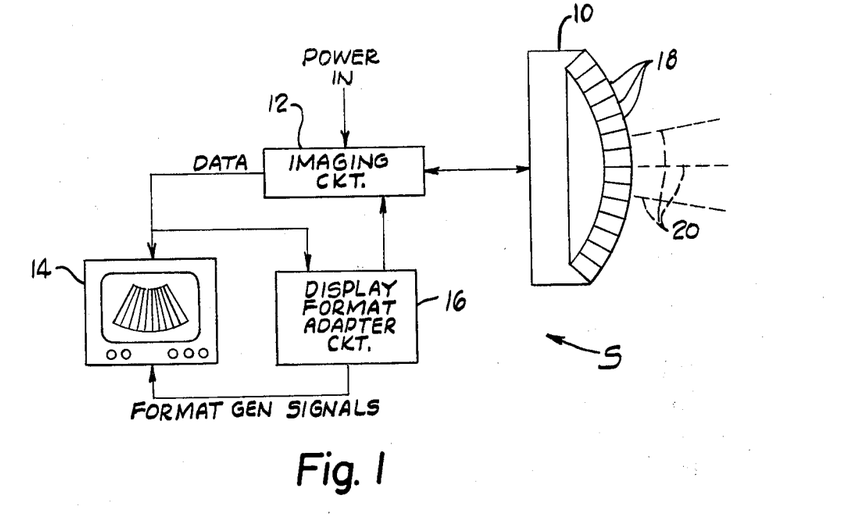
FIG. 1 is a generalized block diagram illustrating an ultrasonic examination system incorporating the present invention.

FIG. 1 illustrates in general form a system S incorporating the present invention. The system S directs ultrasonic energy into a subject, such as a patient's body, and in response to echoes produced by the incident energy, produces an image representing internal structure or condition of the body.

The system S includes a curvilinear transducer assembly 10 for producing incident ultrasonic energy and for receiving echoes thereby caused. Imaging circuitry 12 actuates the transducer assembly to produce the incident energy, and receives electrical signals from the transducer produced in response to the echoes. Data from the imaging circuitry, in the form of these elecrical signals, is directed to a display apparatus 14 which produces the image. Display format adapter circuitry 16 provides format generating signals to the display apparatus 14, defining an array of image lines constituting the image, in response to data and timing control signals received from the imaging circuitry 12.

The transducer assembly 10 preferably includes 76 individual transducer elements, such as indicated by the reference character 18. Each transducer element comprises an individual piezoelectric ultrasonic transducer of known type, having a particular axis along which ultrasonic energy from the element is primarily directed. The ultrasonic transducer elements 18 are arranged in a curvilinear disposition along a circular arc. The axes of transmission of the elements, such as indicated by the dotted lines 20 in FIG. 1, diverge radially from the imaginary center of the circle defined by the arc along which the transducer elements are arranged.

In this preferred embodiment, the radius of curvature of the arc along which the transducer elements are disposed is approximately 10 centimeters (cm). The arcuate length of the transducer element array is approximately 5 centimeters.

The imaging circuitry actuates the transducer elements to produce short bursts of ultrasonic energy, each burst having a frequency of approximately 3.5 megahertz (MHz.). The imaging circuitry actuates a sequence of groups of transducer elements 18 such that resultant ultrasonic beams transmitted from the transducer assembly 10 scan the subject body in a sequence of different angles relative to the transducer assembly. This mode of scanning is of known type, and is sometimes referred to as "real time stepped ultrasonic scanning".

Echoes returning from tissue interfaces within the patient's body cause the transducer elements to produce electrical signals representing characteristics of those echoes. These electrical signals are received and processed by the imaging circuitry, which then directs them as data signals to the display apparatus 14, which may preferably comprise a cathode ray tube (CRT) display apparatus.

Preferably, the imaging circuitry 12 actuates or "fires" successive groups of 16 transducer elements each. The imaging circuitry 12 fires each group of transducers in a phased delay fashion, such that incident ultrasonic energy produced by the transducer assembly 10 is focussed at a distance of approximately 4 centimeters from the transducer assembly. Additionally, the receiving periods of the members of each group of transducers are delayed in varying amounts in order to focus the zone from which echoes are received most readily at a distance of approximately 6 centimeters from the transducer assembly. These focusing delay characteristics are described in more detail below.

Display format adaptor circuitry 16 receives data and timing signals from the imaging circuitry 12, and produces format generating signals for causing the display apparatus 14 to produce a display comprising a number of divergent image lines collectively arranged in the form of radii of a truncated annulus. The arcuate length of the inner portion of the annulus display area (skin level) is approximately 5 centimeters, and the corresponding distance, or width, at the outer edge of the annulus (corresponding to the maximum range of about 20 cm.) is approximately 15 centimeters. Where the interior edge of the truncated annulus is located at the patient's skin line, the range of system operations is approximately 20 centimeters into the body. The included angle of the truncated annulus is approximately 30 degrees.

Figure 2:
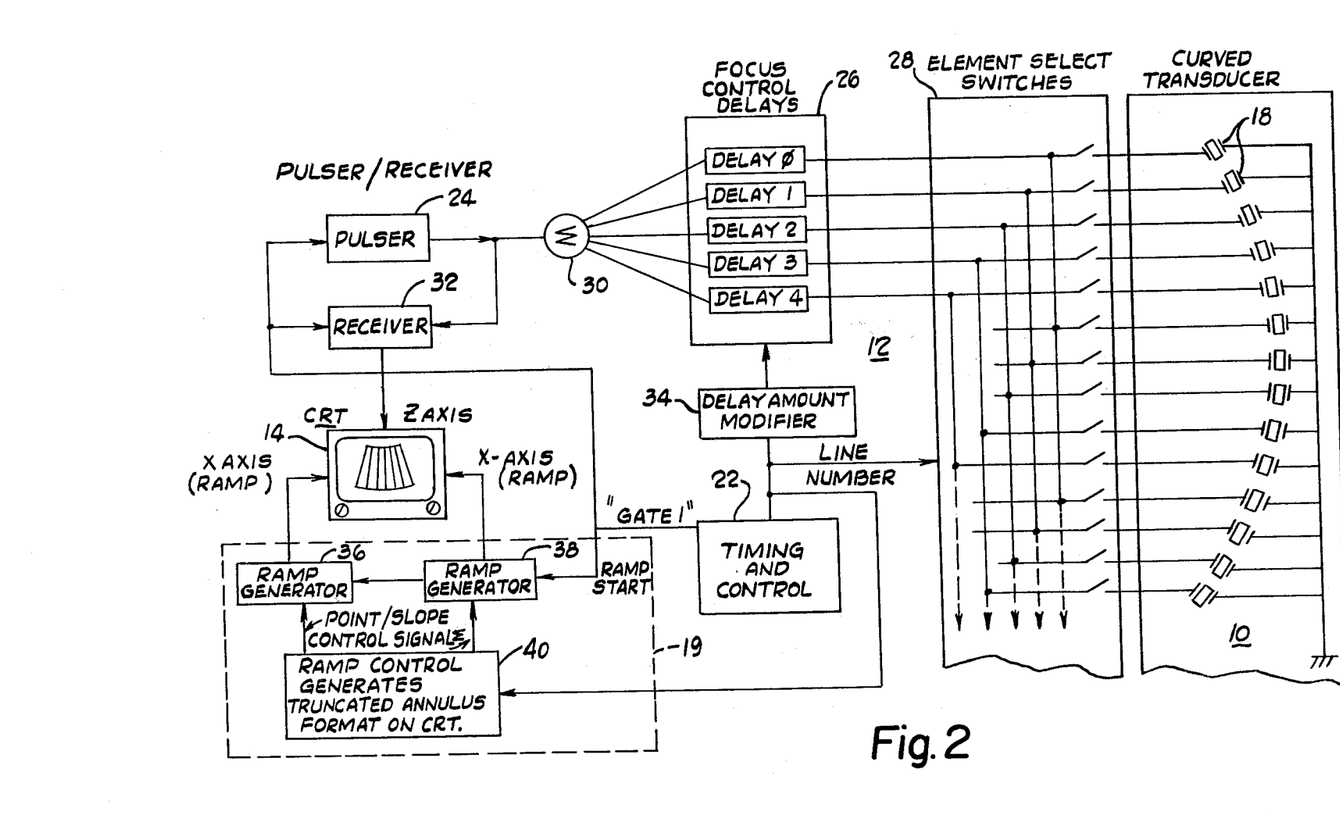
FIG. 2 is more detailed block diagram illustrating the system more generally exhibited in FIG. 1.

FIG. 2 illustrates in more detail an embodiment of an ultrasonic examination system incorporating the present invention. The imaging circuitry 12 includes timing and control circuitry 22 which sequences the operation of the remainder of the system S. The timing circuitry 22 actuates pulser circuitry 24 to fire the appropriate groups of transducer elements 18. Electrical signals from the pulsers 24 are transmitted along respective parallel signal channels to actuate the transducer elements 18 by way of delay control circuitry 26 and switching circuitry 28.

The switching circuitry 28 is controlled by the timing circuitry 22 to close appropriate members of the switching circuitry in order to govern the sequence of actuation of the transducer elements 18. Likewise, the focusing delay circuitry 26 is controlled by the timing and control circuitry 22 to impose delays on the various channels into which the pulser produces the actuation signals.

When echoes return to the respective transducer elements 18 which have been fired, the transducer elements convert the echoes to respective electrical signals. These received signals are transmitted back over each of the respective channels by way of the switching circuitry 28 and focus delay circuitry 26.

The focusing delay circuitry is controlled in the receive mode by the timing and control circuitry 22 to impose receiving delays upon the received signals. These receiving delays focus the receiving zone of the transducer elements 18 in phase delay fashion to enhance sensitivity of the system to echoes generated in a particular reception zone relative to the transducer position.

The received and delayed signals are passed through a summing circuit 30 and directed to receiver circuitry 32. The receiver circuitry 32 transmits the summed received signals to the "Z," or intensity control, input of the display apparatus 14, which preferably is embodied by a cathode ray tube device.

Delay modification circuitry 34, described in more detail below, is provided between the timing and control circuitry 22 and the delay focusing circuitry 26. The delay modification circuitry controls the delays interposed by the various delay elements in each channel, during both the transmit and receive modes, in order to impose the proper focusing delays on the various signals, taking into account the curvature of the transducer assembly 10.

The pulser, receiver, and summing circuitry, as well as the focusing delay circuitry, switching circuitry and timing and control circuitry are exemplified for example in the analogous circuitry of an ultrasonic examination system, Model LS1000, sold by Picker Corporation, Northford, Conn., U.S.A.

The display format adaptor circuitry 19 includes a pair of ramp generators 36, 38 and ramp control circuitry 40. The outputs of the ramp generators 36, 38 are coupled to the Y axis and X axis inputs, respectively, of the display apparatus 14. By proper adjustment by the ramp control circuit of the starting times, initial values, and slopes of the ramp signals produced by the ramp generators, an array of divergent radii having a common center can be generated on the screen of the display apparatus. As shown in FIG. 2, this array of lines provides a display in the format of a truncated annulus. Each of the divergent radii on the display corresponds in location to a respective one of the divergent ultrasonic beams generated in sequence by the transducer assembly 10.

Thus, the system produces a display in the form of a truncated annulus whose interior edge represents the patient's skin surface, at the face of the transducer assembly, and whose outer edge represents the maximum range of the system field of view. The use of the curvilinear transducer assembly, with its corresponding truncated annular display, provides a much larger field of view than was previously obtainable by the use of a linear transducer assembly having the same length of that of the noval curvilinear transducer assembly. This larger field of view is obtainable without the aid of electronic delay circuitry for changing the incident angle of the produced ultrasonic energy. The larger field is likewise obtainable without the use of mechanical sector scanning techniques which can be expensive and cumbersome.

In operation, the two ramp signals defining the slope of each line component of the display format are initiated in response to a signal appearing on the lead indicated "ramp start." The ramp start signal is produced by the timing and control circuitry 22, and is timed to be synchronized relative to the firing of the transducer elements by the pulser cirucitry 24. The ramp control circuitry 40 is controlled by a signal from the timing and control circuitry 22 appearing on the "line number" lead which identifies the particular radial line component of the image to be generated in response to information derived from the current firing of the pulser circuitry 24.

Preferably, the transducers are fired in groups of 16, and the pulser and delay circuitry correspondingly define 16 electrical channels. The system is operated to produce real time images at approximately 30 frames per second. Each image preferably comprises 120 lines.

A 120 line image can be obtained, if desired, from a 76 element transducer assembly by the employment of known fractional stepping techniques, such as described in the following publication which is hereby expressly incorporated by reference: Yoshikawa, Y. et al., "Scanning Methods in Electro-Scanning Ultrasonic Diagnostic Equipment."

As noted above, the incident ultrasonic energy produced in the transmit mode is focused by phase delay technique at 4 centimeters from the transducer array. The delay program for accomplishing this focusing, taking into account transducer array curvature, is defined in Table I:

| Transducer Group Elements | Delay (Nanoseconds) |
| --- | --- |
| 1 and 16 | 0 |
| 2 and 15 | 113 |
| 3 and 14 | 210 |
| 4 and 13 | 290 |
| 5 and 12 | 355 |
| 6 and 11 | 403 |
| 7 and 10 | 437 |
| 8 and 9 | 453 |

Similarly, the reception focal zone is focused at approximately 6 centimeters from the transducer array. The delay program for accomplishing this delay in the receive mode is defined by the following Table II:

| Transducer Group Elements | Delay (Nanoseconds) |
| --- | --- |
| 1 and 16 | 347 |
| 2 and 15 | 261 |
| 3 and 14 | 187 |
| 4 and 13 | 125 |
| 5 and 12 | 75 |
| 6 and 11 | 38 |
| 7 and 10 | 13 |
| 8 and 9 | 0 |

Figure 3:
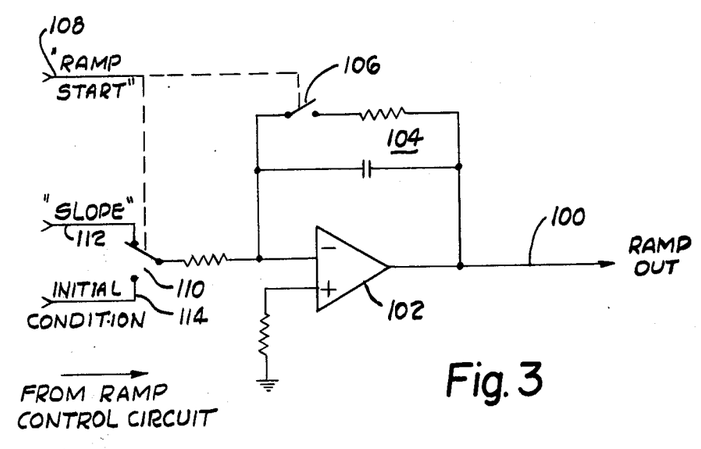
FIGS. 3-4 are schematic drawings illustrating portions of the system shown in block form in FIG. 2.
Figure 4:
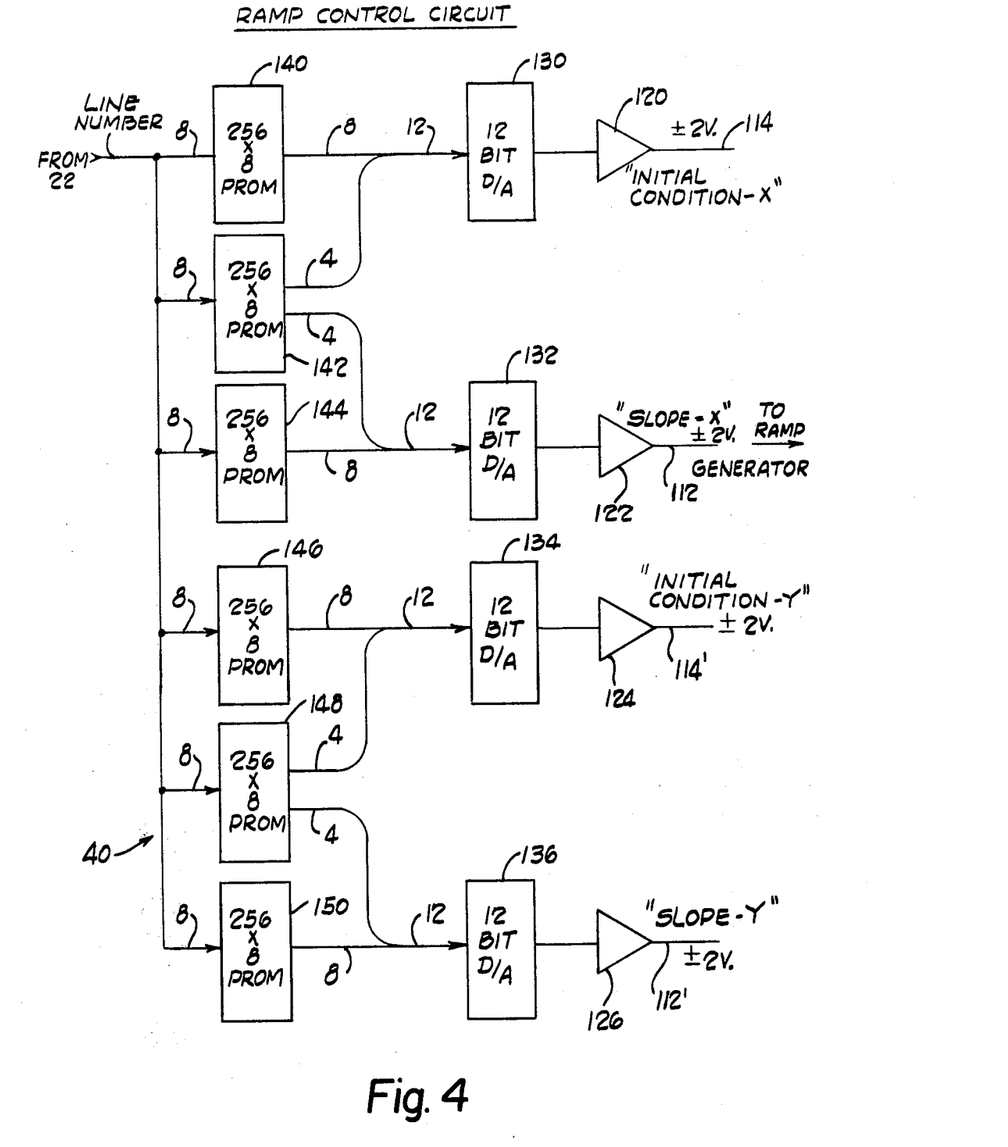

FIGS. 3 and 4 illustrate in schematic form the circuitry embodying the ramp generators 36, 38 and the ramp control circuitry control 40.

FIG. 3 shows the schematic diagram of a ramp generator circuit. The ramp generator circuit of FIG. 3 corresponds to either of the ramp generator circuits 36, 38, their circuitry being identical. For purposes of simplicity, only one such ramp generator circuit is illustrated in detail.

The ramp generator circuit produces a ramp output voltage signal at a lead 100 which is the output of operational amplifier 102. Control over the ramp characteristics is influenced by the RC circuit 104 coupled between input and output of the amplifier 102. Closure of a switch 106 in the circuit 104 initiates production of the ramp signal. The switch 106 is closed by way of a signal appearing on "ramp start" input 108, generated by timing control circuitry 22.

Other signals, from the ramp control circuitry 40, govern aspects of the ramp signals generated at the lead 100. More specifically, a signal on a lead 112 defines the slope of the ramp signal generated. Another signal from the ramp control circuitry 40, appearing at a lead 114, governs the inital value of the ramp at its starting time.

Signals on the leads 112, 114 are input to the operational amplifier 102 by way of a two-position switch 110. The condition of the signal on the lead 108 controls the position of the switch 110. Prior to the initiation of the ramp signal output, the switch 110 is in its lower position, such that it defines the initial ramp signal value. Upon initiation of ramp signal production, the switch 110 is moved to its upper position, such that the ramp slope information input on the lead 112 is then applied to the operational amplifier 102, to control ramp slope.

The ramp generators 36, 38, conjunctively define the X-Y location of each radial image display line generated on the display screen. The ramp generators govern both the starting and ending position of each display image line, and its slope or path on the screen. The ramp generators perform this function by application of the ramp signals to the X and Y deflection plates, respectively, of the display CRT.

The slope of the actual display image line is a function of the ratio of the slopes of the respective ramp signals produced by the generators 36, 38. Thus, the slope of the image line displayed is distinct from, but a function of, the slopes of the individual ramp signals produced by the generators 36, 38.

The initial position of the trace of the image display line is determined by the initial values of the ramp signals produced by the two generators. Each initial position, in known fashion, provides the X-Y coordinate location of the beginning point of the corresponding image display line.

FIG. 4 illustrates in schematic form a preferable embodiment of the ramp control circuitry 40. The ramp control circuitry produces four outputs, two outputs directed to each of the ramp generator circuits 36, 38. The ramp control circuit outputs to each ramp generator an analog signal indicating the initial value of the ramp to be generated and the slope of that ramp. These signals are produced in response to a digital signal from the timing and control circuitry 22 indicating by number the particular image display line which is to be generated by the next ramp signals produced.

More specifically, signals appearing at the outputs 114, 112 indicate the initial value and slope, respectively, of the ramp signals to be produced by the ramp generator 38 for the image display line under consideration. Similarly, signals at the leads 114' and 112' define the analogous parameters for the Y axis ramp signal to be generated by the generator circuit 36.

The outputs on leads 114, 114' 112, 112' are produced by the operational amplifiers 120, 122, 124 and 126 as indicated in FIG. 4.

These operational amplifiers are fed input signals from the output of digital to analog converters, 130, 132, 134, 136, respectively. The inputs to the digital to analog converters are supplied as digital outputs from a series of six PROMS (programmable read only memories) 140, 142, 144, 146, 148, 150. The function of the PROM circuits is to receive a digital input identifying the line number of the individual display line to be produced in response to the immediately subsequent action of the ramp control circuitry 40. In response to each line number input to the PROMS, each PROM produces a preprogrammed unique diital signal, The PROMS are programmed such that their digital signal outputs, as they are clocked by the "line number" digital signal, establish the proper initial conditions, ramp slopes and ramp timing to generate on the display the appropriate corresponding image line.

Figure 5:
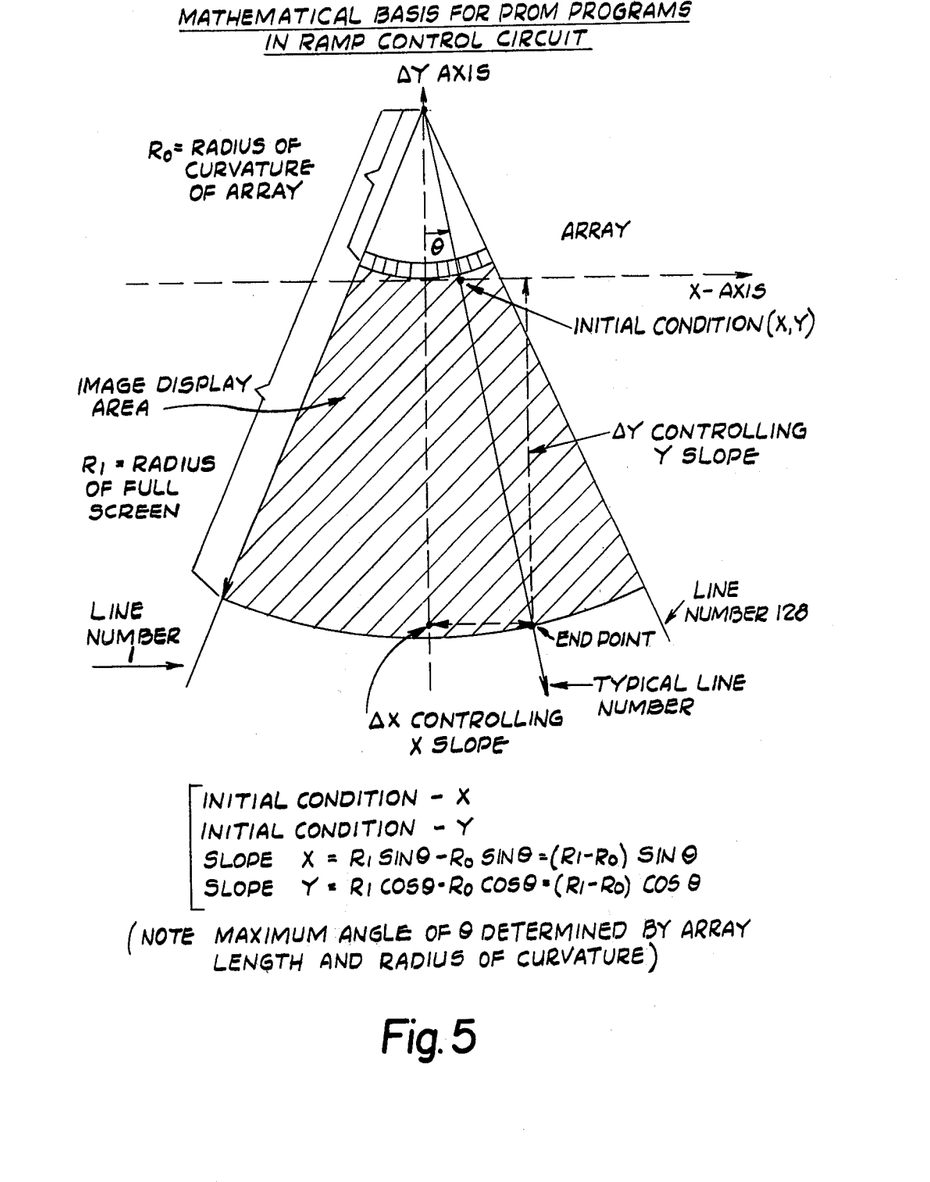
FIG. 5 is a graphical drawing illustrating mathematical parameters of components of the system shown in FIG. 2.

It is believed that those of ordinary skill in the art relevant to the subject matter discussed here would be able, by the use of ordinary trigonometry to provide appropriate programming for the PROMS by analyzing the geometry of each desired image display line individually. However, for those not intimately familiar with this art, FIG. 5 is provided, illustrating the mathematical consideration involved in programming the PROM to generate appropriate initial conditions and slopes for each respective display line. In the embodiment described in FIG. 5, the display is configured as a truncated annulus having several individual display lines. The angle $\theta$ varies in increments equal to the total angular excursion of the display area divided by the number of lines. The equations for programming each output for the PROMS corresponding to each individual display image line, are set forth near the bottom of FIG. 5. The initial conditions and slopes for both X and Y are determinable by substituting for $\theta$ each individual angle of each display image line which is desired to be produced. The embodiment of the display format adapter circuitry 16 described above comprises analog circuitry. As a matter of choice, however, those of ordinary skill in the art may embody the display format adapter circuitry 16 in a digital form.

Figure 6:
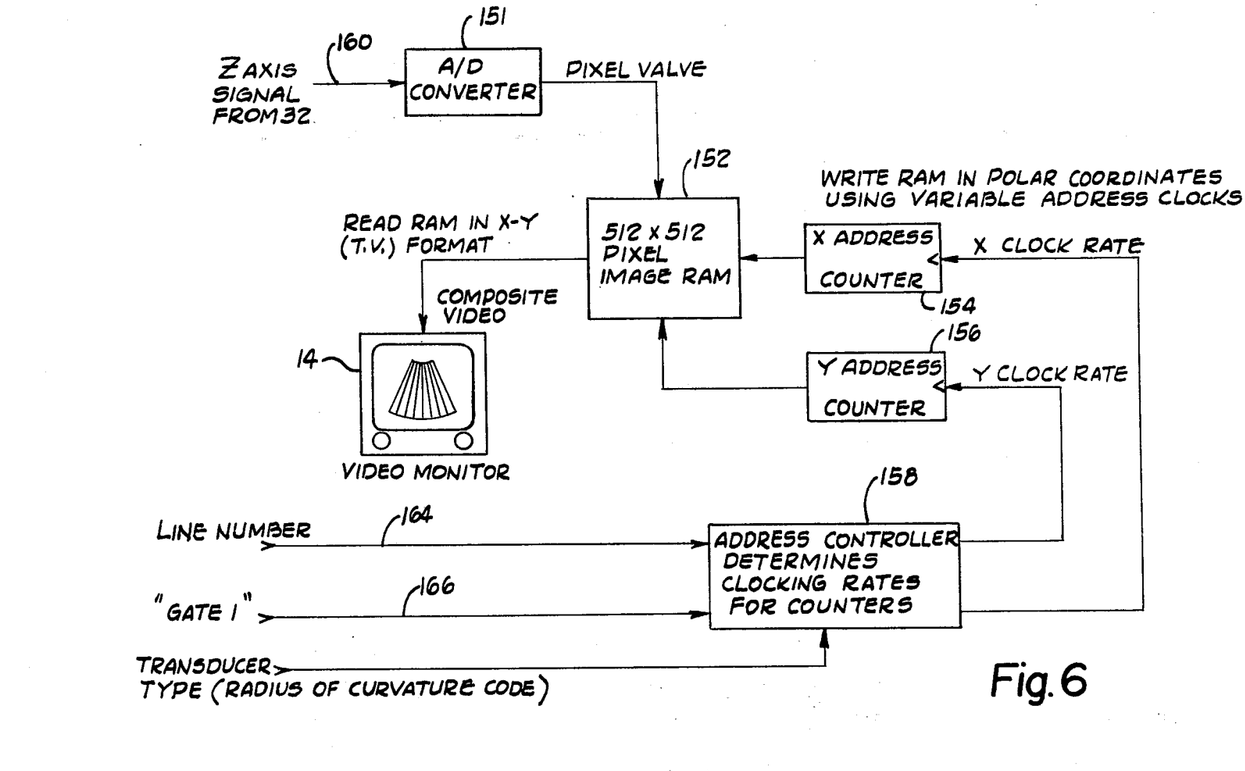
FIG. 6 is a block diagram illustrating an alternative embodiment portion of the system of FIG. 2.

More specifically, such an embodiment could suitably comprise an ESS digital scan coverter. A suggested embodiment for such a digital scan converter is illustrated in FIG. 6. The scan converter of FIG. 6 comprises an analog to digital converter 151, a random access memory 152, address counter circuitry 154, 156 and address counter control circuitry 158.

In operation, the "Z" signal from the receiver circuitry, appearing upon a lead 160, is converted to digital form by the converter 151 and presented to the random access memory (RAM). The address counters and counter control circuitry determine the address in the RAM at which the incoming digitized Z signal is to be placed. The address counters 154, 156 are used to write the RAM in polar coordinates. The counters are operated by variable address clock rate signals from the counter control circuitry 158. The counter control circuitry 158 operates in response to signals from the timing and control circuitry 22 appearing on the leads 164, 166. The signal on the lead 166 indicates the particular line of the composite image to be currently displayed. The signal on the lead 166 is a synchronizing signal to synchronize the production of the displayed line relative to the firing of the transducers.

When a digital representation of an image frame has been accumulated in the RAM by steering the incoming digitized Z axis signals among the appropriate RAM addresses, the RAM contents are read out in XY television format, and presented as inputs to a CRT video monitor display apparatus 14.

It should be kept in mind that the foregoing disclosure is intended to be illustrative, rather than exhaustive, of the invention. Those of ordinary skill in the pertinent art may be able to make additions, deletions, or modifications to the preferred embodiment described above without departing from the spirit or scope of the invention, as defined in the appended claims.

We claim:

1. An ultrasonic medical diagnostic contact scanner for producing an image of a patient's internal body structure, said system comprising:
   (a) a transducer assembly comprising:
      (i) a non-cylindrical convex curvilinear array of ultrasonic transducer elements defining an array of respective corresponding coplanar divergent axes of ultrasonic emission along each of which axes ultrasonic energy from the corresponding element is primarily directed;
(ii) said curvilinear transducer assembly configured to describe substantially an arc of a circle of arcuate length encompassing less than one-fourth of said circle and having a radius of curvature of at least five centimeters;
(iii) the arcuate length of said transducer array being much greater than its width;
(iv) said assembly being dimensioned to facilitate imposition of all of said transducer elements simultaneously in contact with a patient's abdomen;
(v) said transducer assembly being further dimensioned to facilitate hand holding of the assembly;
(b) imaging electronics for causing sub-groups of the transducer elements, each of said sub-groups comprising a plurality of, but less than all, of said elements, to emit incident ultrasonic energy into the patient in an electronically step scanned sequence of discrete beams and to convert received echoes caused by the incident energy to electrical signals representing internal body structure of the patient, and
(c) a display system responsive to the electrical signals for producing a visual image of patient internal body structure.

2. An ultrasonic medical diagnostic contact scanner for producing an image of a patient's internal body structure, said system comprising:
(a) a transducer assembly comprising:
(i) an elongate non-cylindrical convex curvilinear array of ultrasonic transducer elements having coplanar divergent axes of ultrasonic emission none of said axes diverging by more than 90 degrees from any other of said axes;
(ii) said assembly being dimensioned to facilitate imposition of all of said transducer elements simultaneously in contact with a portion of a patient's body, such as the abdomen;
(b) imaging electronics for causing sub-groups of the transducer elements, said sub-groups comprising less than all of said elements, to emit incident ultrasonic energy into the patient in a real time electronic step scanning sequence and to convert received echoes caused by the incident energy to electrical signals representing internal body structure of the patient, and
(c) a display system responsive to the electrical signals for producing a real time visual image of a plane extending through the patient's body.

3. An ultrasonic medical diagnostic contact scanner for producing an image of a patient's internal body structure, said system comprising:
(a) a transducer assembly comprising:
(i) a non-cylindrical convex curvilinear array of ultrasonic transducer elements having coplanar divergent axes of ultrasonic emission;
(ii) said curvilinear transducer assembly having a radius of curvature of at least one centimeter;
(ii) the length of said transducer array being much greater than its width and at least about 5 centimeters;
(b) imaging electronics for causing sub-groups of the transducer elements, said sub-groups comprising a plurality of, but less than all, of said elements, to electronically scan incident ultrasonic energy through the patient in a sequence and to convert received echoes caused by the incident energy to electrical signals representing internal body structure of the patient, and
(c) a display system responsive to the electrical signals for producing a visual real time image of the patient's internal body structure.

4. An ultrasonic medical diagnostic system comprising:
(a) a hand-held stationary surface sector scanning assembly comprising an array of ultrasonic transducer elements having a fixed elongate convex curvilinear configuration, each of said elements having an emitting face defining a central axis, none of said axes diverging from any other by more than about 90°, said array being dimensioned and configured for simultaneous imposition of each of said elements against the exterior of a patient's body;
(b) imaging electronics for actuating respective sub-groups of said elements in a sequence to electrically scan incident ultrasonic energy in discrete resultant beams through a patient and to produce electrical signals from echoes of said incident energy, and
(c) a display system responsive to the electrical signals for producing a tangible representation of internal structure of the patient into which the energy is directed.

5. An ultrasonic medical diagnostic contact scanner for producing an image of a patient's internal body structure, said system comprising:
(a) a transducer assembly comprising:
(i) a convex curvilinear array of ultrasonic transducer elements having divergent axes of ultrasonic transmission and reception of ultrasonic energy, said axes being coplanar and intersecting at a point proximate the center of curvature of the array;
(ii) said curvilinear transducer assembly configured to describe an arc of a circle of arcuate length encompassing less than one-fourth of said circle and having a radius of curvature of at least 5 centimeters;
(iii) the circumferential length of said transducer array along said arc being much greater than the width dimension of the transducer array as defined in a direction normal to the plane defined by the transmission axes;
(iv) said assembly being dimensioned to facilitate imposition of all of said transducer elements simultaneously in contact with a human patient's abdomen;
(v) said transducer assembly being further dimensioned to facilitate hand holding of the assembly;
(b) imaging electronics for causing sub-groups of the transducer elements, each of said sub-groups comprising a plurality of, but less than all, of said elements, to emit incident ultrasonic energy into the patient in an electronically step scanned sequence of discrete beams and to convert received echoes caused by the incident energy to electrical signals representing internal body structure of the patient, and
(c) a display system responsive to the electrical signals for producing a visual image of patient internal body structure.

* * * * *